United States Patent [19]
Fortier et al.

[11] Patent Number: 5,972,009
[45] Date of Patent: Oct. 26, 1999

[54] LIGATING BAND WITH ROUNDED EDGES AND METHOD OF USE OF SAME

[75] Inventors: Richard C. Fortier, Concord; Susan M. Ostrowski, Arlington, both of Mass.

[73] Assignee: Boston Scientific Corporation, Natick, Mass.

[21] Appl. No.: 09/056,575

[22] Filed: Apr. 7, 1998

[51] Int. Cl.$^6$ ..................................................... A61B 17/08
[52] U.S. Cl. .......................... 606/157; 606/158; 606/151
[58] Field of Search ................................... 606/151, 157, 606/158; 128/831; 206/805

[56] References Cited

U.S. PATENT DOCUMENTS

| | | | |
|---|---|---|---|
| 3,880,166 | 4/1975 | Fogarty | 128/325 |
| 4,167,188 | 9/1979 | Lay et al. | 128/326 |
| 4,794,927 | 1/1989 | Yoon | 128/326 |
| 4,881,939 | 11/1989 | Newman | 606/31 |
| 5,074,869 | 12/1991 | Daicoff | 606/158 |
| 5,702,411 | 12/1997 | Back et al. | 606/157 |
| 5,752,966 | 5/1998 | Chang | 606/151 |

*Primary Examiner*—Michael Buiz
*Assistant Examiner*—Tina T. D. Pham
*Attorney, Agent, or Firm*—Kenyon & Kenyon

[57] ABSTRACT

An improved elastic band for ligating tissue within a living body comprises a central opening defining an axis. A first curved edge is formed between a first surface extending substantially parallel to the axis and a second surface extending substantially perpendicular to the axis. A method of ligating tissue within a living body using such a ligating band comprises the steps of positioning the elastic band, which has been stretched to increase the size of a central opening extending therethrough, adjacent to a portion of tissue to be ligated. The tissue to be ligated is then drawn through the central opening of the elastic band and the elastic band is released so that the size of the central opening decreases to grip the tissue received therein.

4 Claims, 8 Drawing Sheets

LIGATING BAND WITH ROUNDED EDGES AND METHOD OF USE OF SAME

CLAIM OF PRIORITY

This application claims priority under 35 U.S.C. Sec. 120 to U.S. patent application Ser. No. 08/866,989, filed Jun. 6, 1997, and assigned to the assignee of the present application. That application is hereby incorporated by reference.

FIELD OF THE INVENTION

The invention relates generally to the field of tissue ligation, and more particularly to an improved ligating band and a method of use of the ligating band to ligate tissue.

BACKGROUND OF THE INVENTION

Physicians have used elastic ligating bands to treat lesions, including internal hemorrhoids and mucositis and for performing mechanical hemostasis.

The object of ligation is to position a ligating band over the targeted lesion or blood vessel section by stretching the band beyond its undeformed diameter drawing the tissue to be ligated within the band and then releasing the band so that it contracts, applying inward pressure on the section of tissue caught within the band. The effect of the inward pressure applied by the band is to stop all circulation through the targeted tissue, thereby causing the tissue to die. The body then sloughs off the dead tissue or the dead tissue may be aspirated into an endoscope or a similar device.

Ligating bands are typically dispensed using ligating band dispensing devices which include cylindrical support surfaces over which elastic ligating bands are stretched. The cylindrical support surfaces arc typically attached to the distal end of an endoscope which is advanced into the body to a target area. A user then applies suction through the endoscope to draw the tissue to be ligated into the cylindrical support surface and then releases a ligating band to contract around the tissue Some ligating band dispensers use trigger lines received in slots at the distal end of a cylindrical support to roll ligating bands toward, and eventually off, the distal end of the support. A problem encountered with such devices when dispensing prior ligating bands is the bands may sometimes slide, rather than roll, along the cylindrical support. A band which slides, rather than rolls, may tend to push the trigger line ahead of it. This is disadvantageous because the trigger line may be pushed out of its slot in the distal rim of the cylindrical support, leaving a band with no trigger line attached.

Ligating bands are often made by extruding an elastic compound through a tubular die. Then tube is then cut transversely to form the bands. As a result of this process, the bands have sharp edges along both the inner and the outer diameter surfaces. Such sharp edges may cause the bands to disadvantageously slide, rather than roll, when being dispensed from devices employing a trigger line.

U.S. Pat. No. 5,356,416 to Chu et al. and U.S. Pat. No. 5,398,844 to Zaslavsky et al., both of which are incorporated herein by reference, describe other types of ligating band dispensing devices which include cylindrical support surfaces over which elastic ligating bands are stretched.

A problem inherent with the type of ligating bands typically used with the above-described devices is that the bands have a tendency to slip off the targeted tissue before the tissue is completely ligated. One reason why a ligating band may slip off targeted tissue is because tissue contained within a ligating band is effectively "pinched" by the ligating band creating an outward pressure on the band. Specifically, the bulb-shaped projection of tissue which has been drawn under suction into the lumen of a cylindrical support surface is pulled away from the surrounding tissue creating tension within the projection which draws the tissue of the projection back toward the its natural position. Thus, the tissue is urged to slip out of the ligating band as the band contracts. In additions blood and fluid within the body can make the surface of the targeted tissue slick, thereby decreasing the coefficient of friction between the ligating band and the targeted tissue. Also, if the targeted tissue is an active blood vessel the "pulsing" effect of blood moving through the vessel can cause the ligating band to slip off of the targeted tissue.

Therefore, what is needed is a ligating band. which rolls, rather than slides, as it moves toward the distal end of the dispenser housing in trigger line-type dispensers. Also what is needed is a ligating band which remains in place once dispensed onto the target tissue.

SUMMARY OF THE INVENTION

The present invention is directed to an improved elastic band for ligating tissue within a living body comprising a central opening defining an axis and having a first curved edge formed between a first surface extending substantially parallel to the axis and a second surface extending substantially perpendicular to the axis.

A method of ligating tissue within a living body using such a ligating band comprises the steps of positioning the elastic band, which has been stretched to increase the size of a central opening extending therethrough, adjacent to a portion of tissue to be ligated. The tissue to be ligated is then drawn through the central opening of the elastic band and the elastic band is released so that the size of the central opening decreases to grip the tissue received therein.

BRIEF DESCRIPTION OF THE DRAWINGS

The invention will be more readily understood through the following detailed description, with reference to the accompanying drawings, in which.

DESCRIPTION OF THE PREFERRED EMBODIMENT

Figure 1:
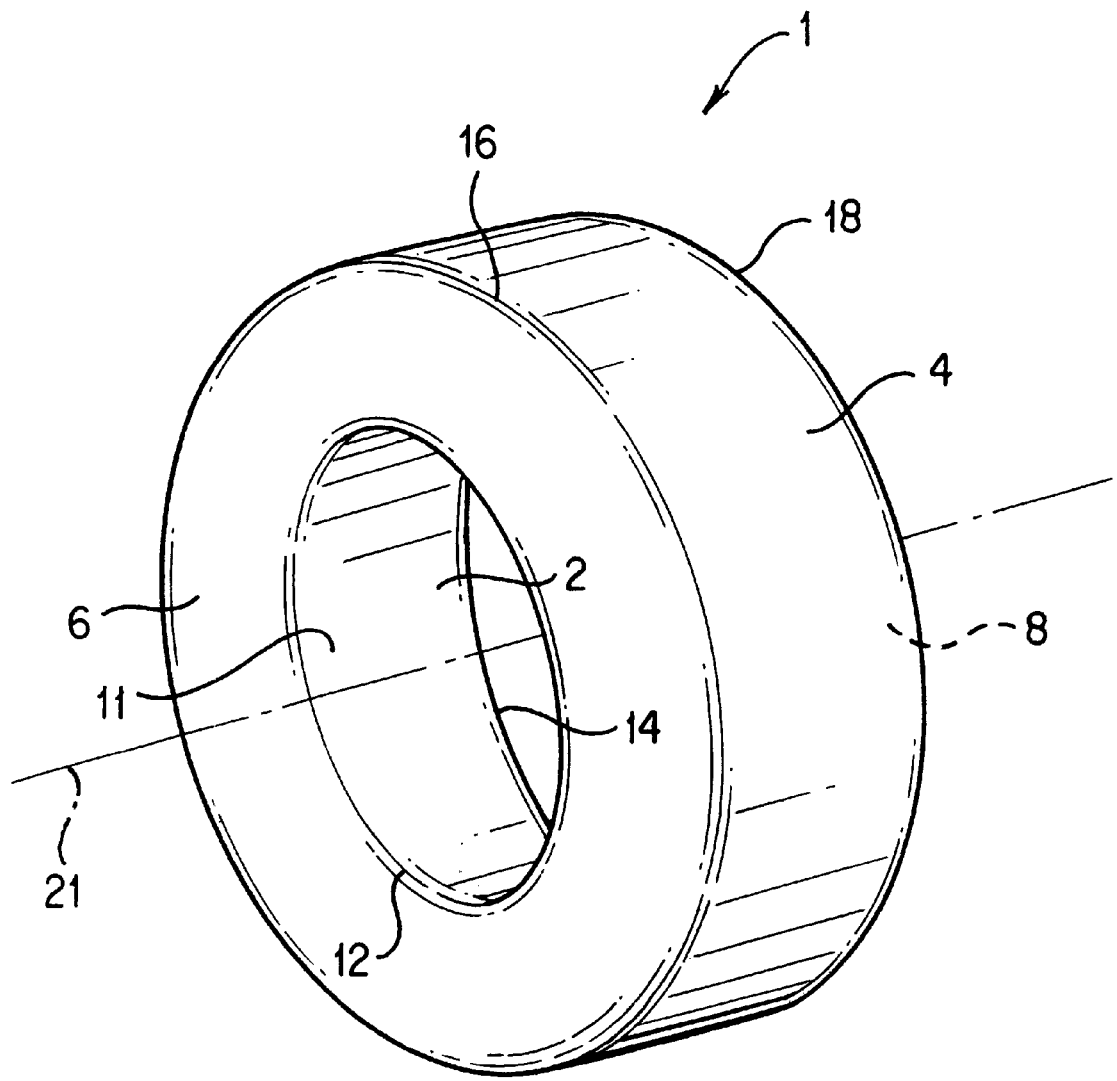
FIG. 1 is a perspective view of a ligating band according to a preferred embodiment of the present invention.
Figure 2:
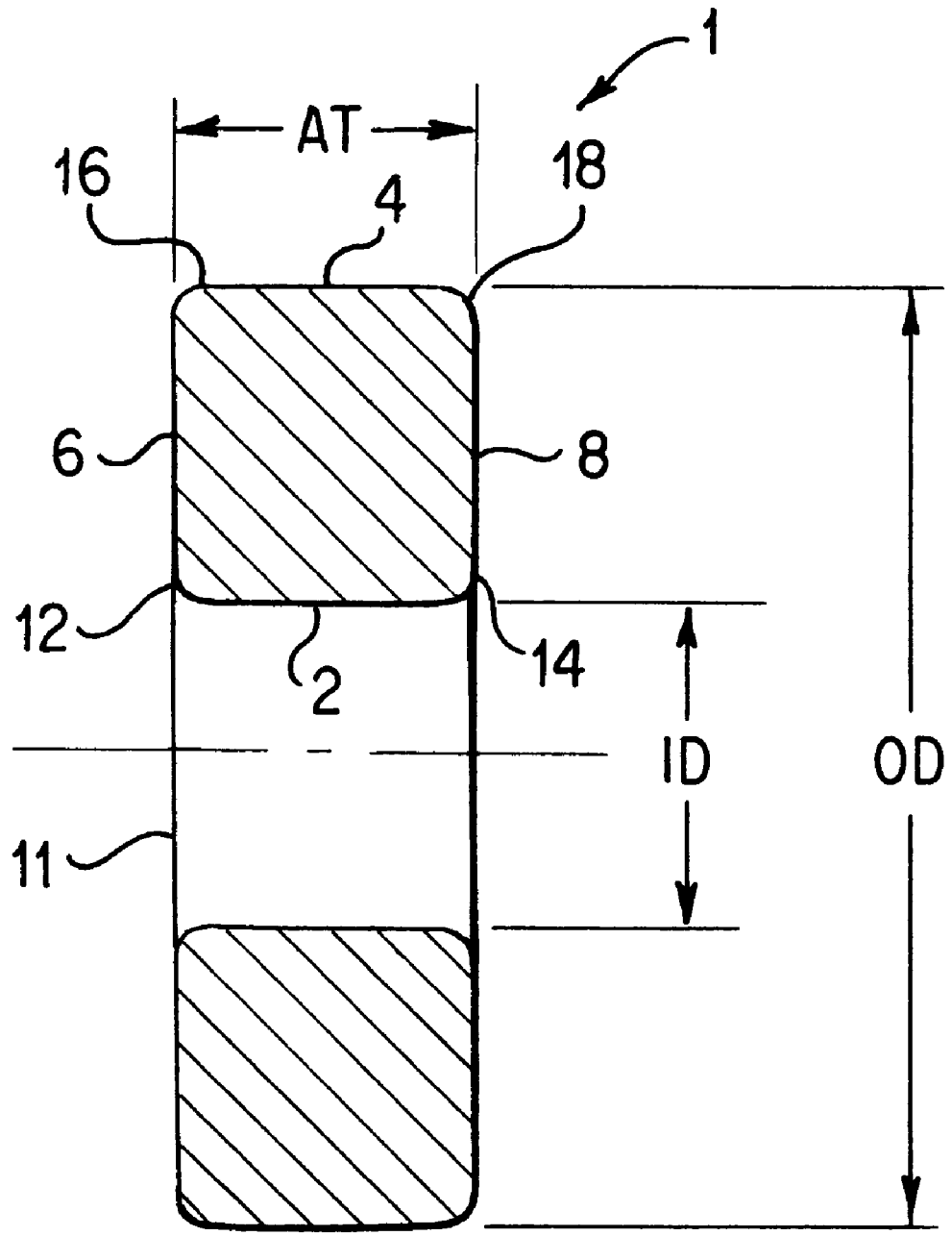
FIG. 2 is an axial cross-sectional view of the ligating band shown in FIG. 1.

A preferred embodiment of the invention is illustrated in FIGS. 1 and 2 as ligating band 1. As embodied herein, ligating band 1 is formed as a ring comprising inner surface 2, outer surface 4, first side surface 6, second side surface 8 and central opening 11 through defining an axis 21. Of course, those skilled in the art will understand that during manipulation, the ligating band 1 may be intentionally or accidentally twisted so that any of the surfaces 4, 6 and 8 becomes the inner surface 2. As embodied herein, surfaces 2 and 6 meet at edge, or juncture, 12. Likewise, surfaces 2 and 8 meet at edge 14, surfaces 4 and 6 meet at edge 16, and surfaces 4 and 8 meet at edge 18. As indicated in FIG. 2, as embodied herein, ligating band 1 has an inner diameter ID, an outer diameter OD, and an axial thickness AT.

As embodied herein, the inner diameter ID of ligating band 1 is between 0.07 and 0.085 inches and is more preferably between 0.07 and 0.08 inches and is most preferably approximately 0.075 inches. The outer diameter OD of the band is preferably between 0.22 and 0.24 inches, while the band preferably has an axial thickness AT of approximately 0.07 and 0.085 inches, is more preferably between 0.07 inches and 0.08 inches and is most preferably approximately 0.075 inches. Of course, those skilled in the art will recognize that such a ligating band may easily be rolled across the cylindrical support surface so that the ID surface becomes the OD surface, etc. and that it may therefore be preferable to make the thickness of the band 1 in each direction between 0.07 and 0.085 inches, more preferably between 0.07 inches and 0.08 inches and most preferably approximately 0.075 inches so that the cross-section of the band 1 is substantially square (except for the rounded edges).

Figure 3:
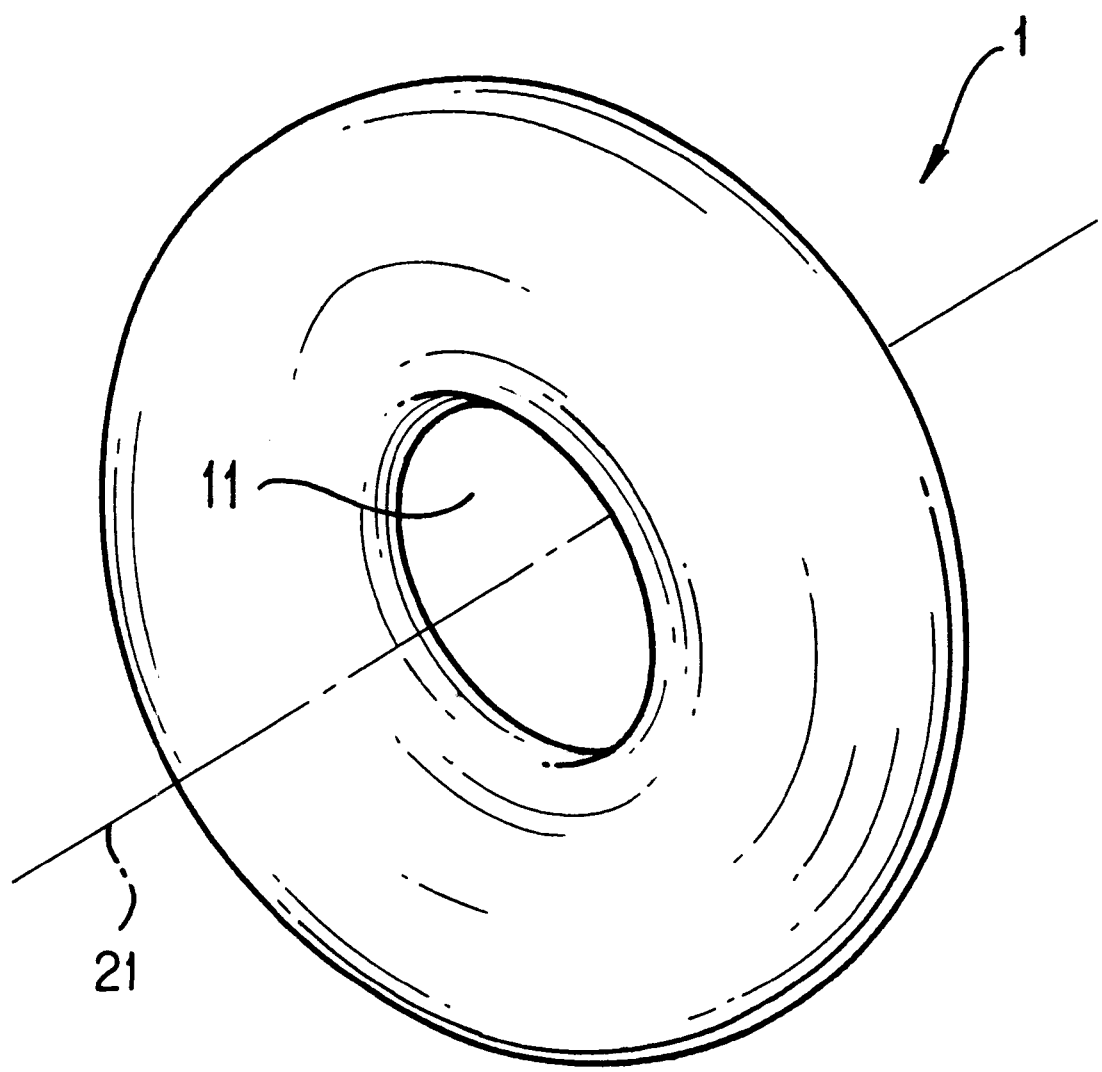
FIG. 3 is a perspective view of a ligating band according to a second embodiment of the present invention.
Figure 4:
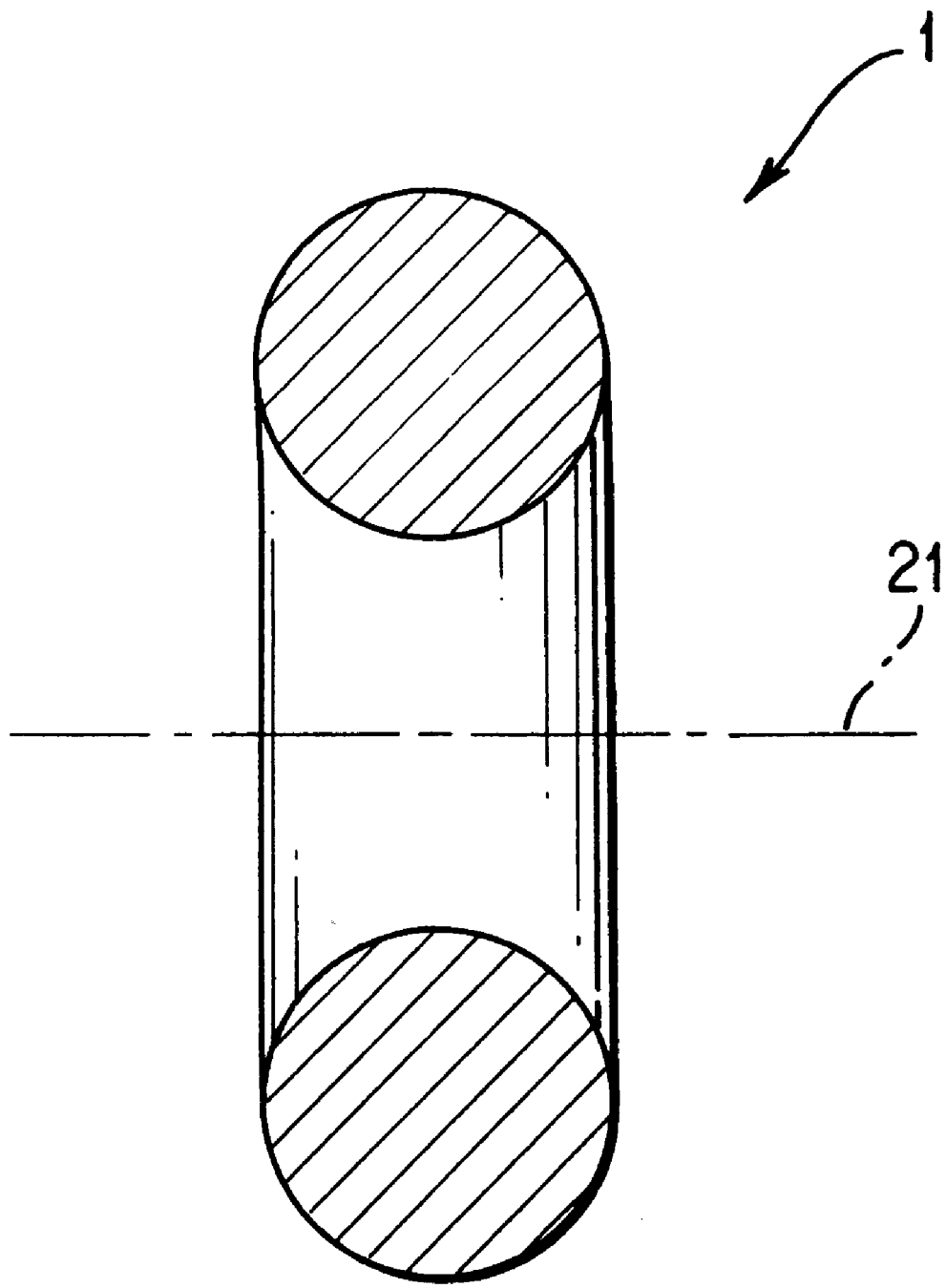
FIG. 4 is a cross-sectional view of the ligating band shown in FIG. 3.
Figure 5:
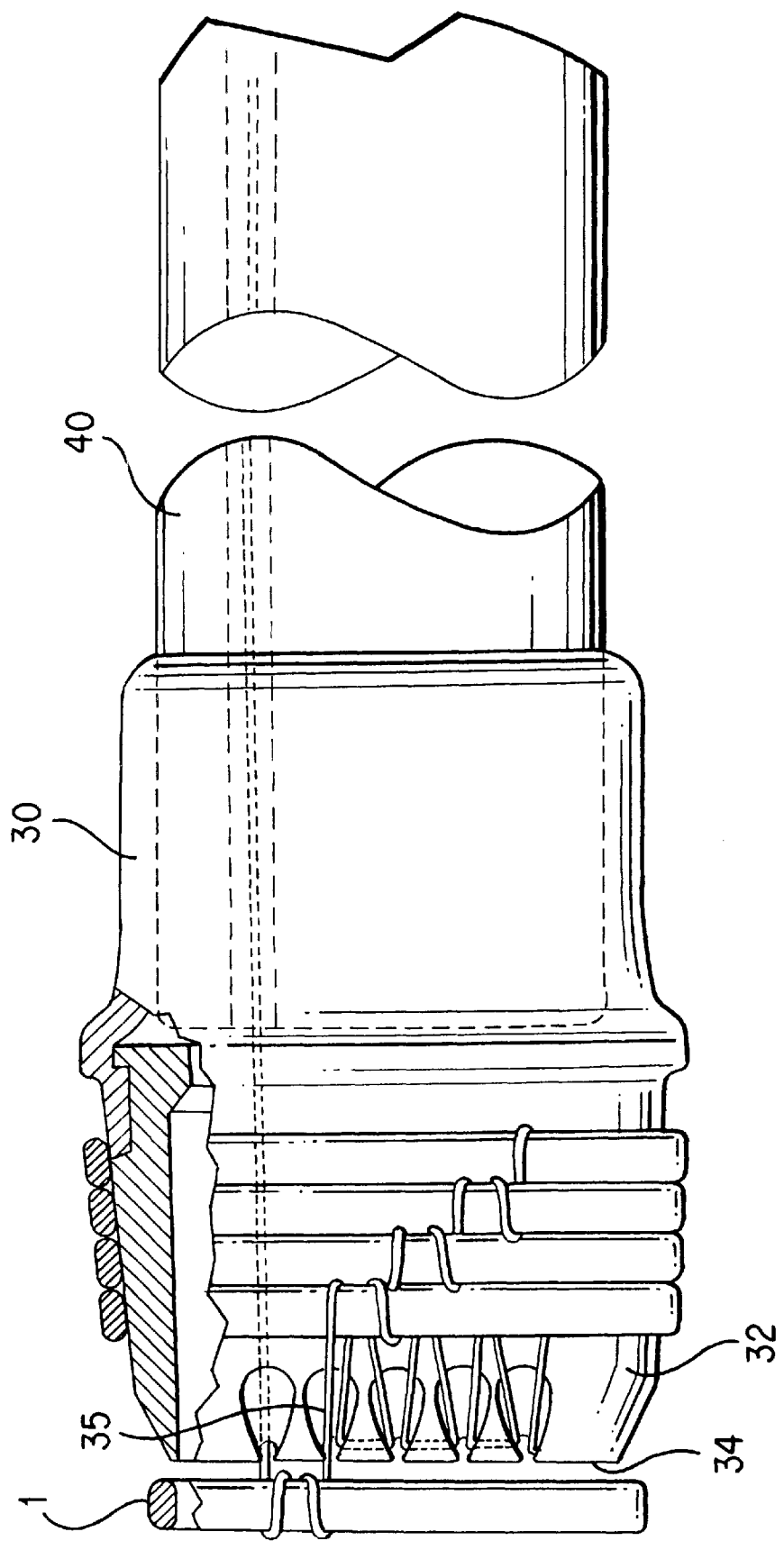
FIG. 5 is a side elevational view in partial cross-section of a prior ligating band dispenser which may be used to dispense a ligating band of the present invention.

As embodied herein, inner surface 2 is preferably substantially parallel to outer surface 4, while first side surface 6 is preferable substantially parallel to second side surface 8, so that ligating band 1 has an axial cross-section which is substantially rectangular. In other embodiments of the invention, surfaces 2 and 4, or 6 and 8, respectively, may be nonparallel to each other so that ligating band 1 has an axial cross-section which is a trapezoid, an irregular quadrilateral, etc. In other embodiments of the invention ligating band 1 may have only three surfaces forming a triangular cross-section. In other embodiments of the invention, some or all of the surfaces 2, 4, 6 and 8 themselves may be rounded. Referring to FIGS. 3 and 4, in yet another embodiment of the invention, surfaces 2. 4, 6 and 8 may be joined so as to form a single continuous surface so that ligating band 1 has a toroidal shape and a substantially circular cross-section. Likewise, in other embodiments of the invention, surfaces 2, 4, 6 and 8 may form a continuous surface having an elliptical or other suitable generally curved cross-section.

Referring again to FIG. 2, as embodied herein, edges 12, 14, 16 and 18 of ligating band 1 are curved, or radiused, so that ligating band 1 may roll when being advanced along a cylindrical support in a ligating band dispenser. Curved edges 12, 14, 16 and 18 may thus avoid the tendency to slide, rather than roll, exhibited by prior ligating bands having sharp edges. As embodied herein the radius of curvature of curved edges 12, 14, 16 and 18 is approximately 0.015 in. for a band having the preferred dimensions described above. In other embodiments of the invention, the radius of curvature of curved edges 12, 14, 16 and 18 may have other appropriate magnitudes apparent to those skilled in the art.

As embodied herein, ligating band 1 is made of from latex. In other embodiments of the invention, ligating band 1 may be made of polyisoprene or any of a variety of other elastic materials. Ligating band 1 is preferably formed by any of a variety of known molding processes such as those in which a material is injected into a mold and cured to form an elastic band of the desired shape and size. In other embodiments of the invention, other band formation techniques known in the art may be employed.

Figure 6:
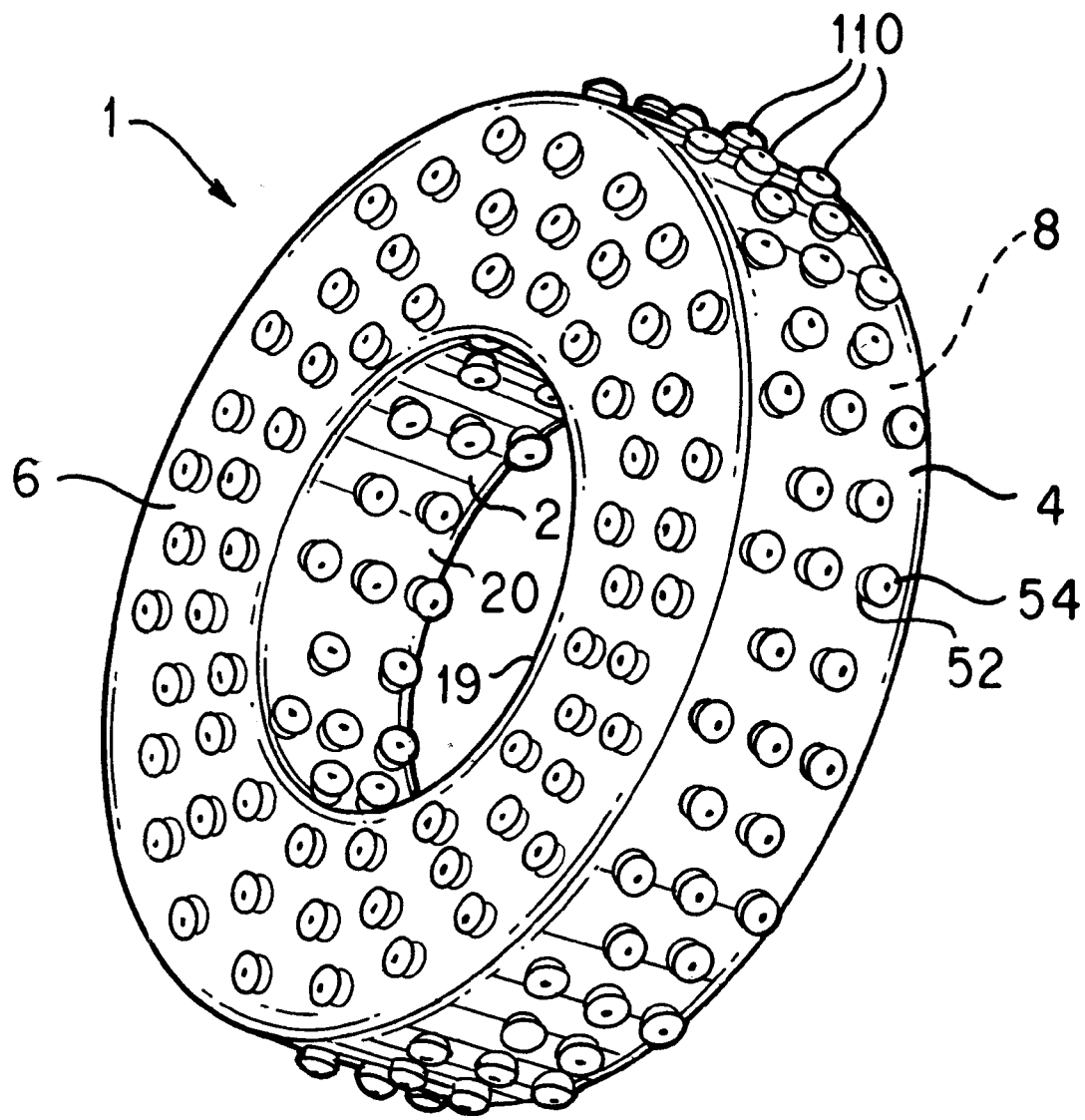
FIG. 6 is a perspective view of a ligating band according to a third embodiment of the present invention having textured surfaces.
Figure 7:
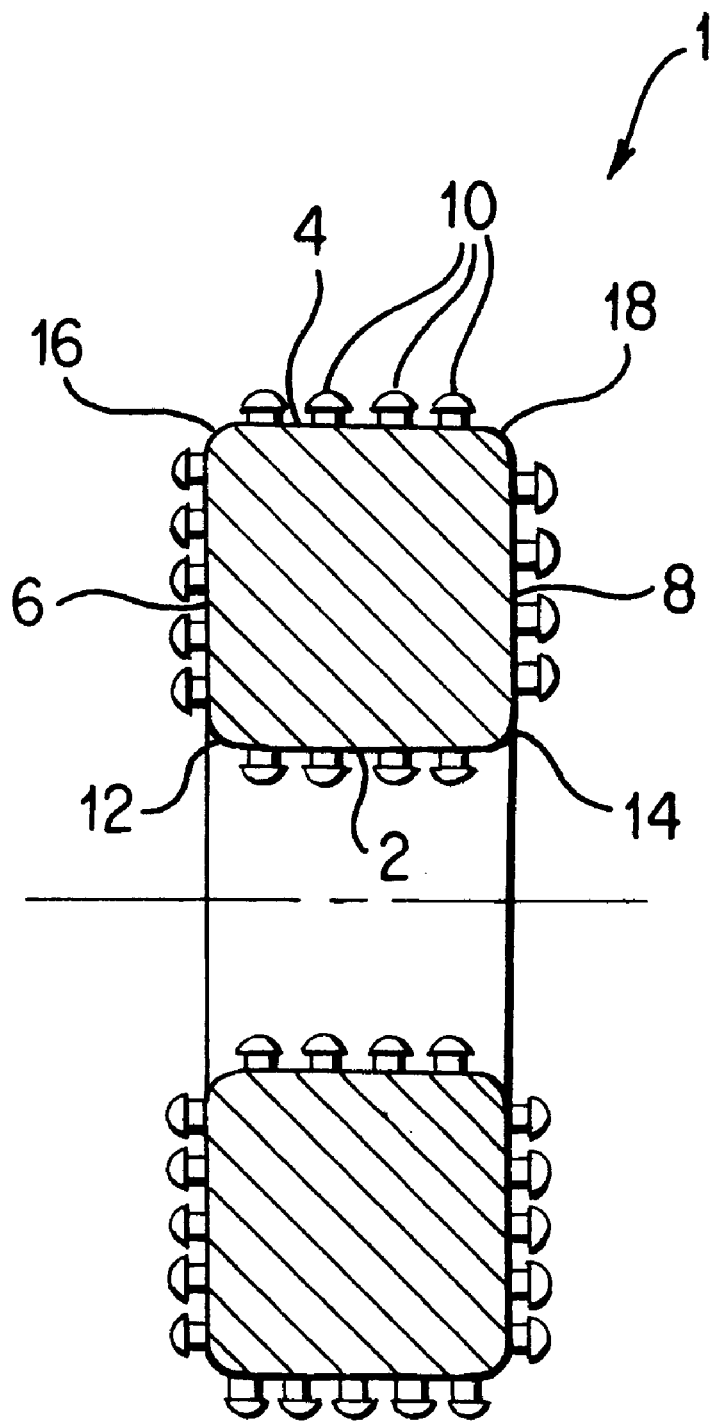
FIG. 7 is a cross-sectional view of the ligating band shown in FIG. 6.

Referring now to FIGS. 6 and 7, in an alternate embodiment of the invention, ligating band 1 is provided with texturing 50, of the type described in U.S. patent application Ser. No. 08/866,989, Texturing 50 provides enhanced gripping of the tissue held by ligating band 1.

As embodied herein, texturing 50 is provided on each surface 2, 4, 6 and 8. In other embodiments, texturing 50 may be provided on all or some of the surfaces of any of the improved ligating band 1 embodiments described herein. Those skilled in the art will recognize that one or more of surfaces 2, 4, 6, or 8 may be rounded, as described above, reducing the distinction between the various surfaces. However, this distinction between the various surfaces is unimportant so long as the surface of the ligating band 1 which is in contact with the tissue to be ligated includes texturing as described herein.

As shown in FIG. 6, the texturing 50 is preferably comprised of a pattern of raised bumps which are formed as cylindrical stems 52 and hemispherical caps 54. In other embodiments of the invention, texturing 50 may comprise other types of discontinuities such as depressions, or both raised bumps and depressions. Alternate forms of texturing 50 can employ one or more of a variety of different shapes. On any surface 2, 4, 6 or 8 to which the texturing 50 is applied, the texturing 50 is preferably evenly distributed.

The texturing 50 may preferably be applied to the ligating band 1 via a molding process, thereby making the texturing 50 an integral part of the structure of the ligating band 1. Preferably, the texturing 50 is formed from the same material as the band itself.

As embodied herein, texturing 50 is applied to the ligating band 1 so that the raised bumps on a first side 18 of the inner surface 2 and the raised bumps on a second side 20 thereof combine to form an interlocking pattern. By interlocking those skilled in the art will understand that the raised bumps on both the first side 19 and the second side 20 hold the tissue to be ligated by the ligating band 1 more securely in place when the ligating band 1 applies inward pressure on the tissue with the bumps from one side forcing the tissue into a gap between the bumps on the other side.

With further reference to FIG. 6, although it is preferable to have texturing 50 on all surfaces 2, 4, 6 and 8 of the ligating band 1, it is not necessarily required so long as the user ensures that the surface including the texturing 50 remains, through the placement procedure, positioned so that it contacts the surface to be ligated. In use, the tissue to be ligated is drawn up within central opening 11. Thus, only texturing 50 placed on the surface positioned at inner surface 2 is designed to come in contact with the tissue to be ligated.

However, it is preferred that texturing 50 be provided on each of surfaces 4, 6 and 8 in addition to inner surface 2 as the ligating band 1 may "roll" after during the dispensing procedure or after being dispensed onto the tissue to be ligated. Thus, a physician cannot be certain that the ligating band 1 will not ultimately be turned "inside out" on the tissue to be ligated such that outer surface 4, for example, comes in contact with the tissue to be ligated rather than the inner surface 2.

Figure 9:
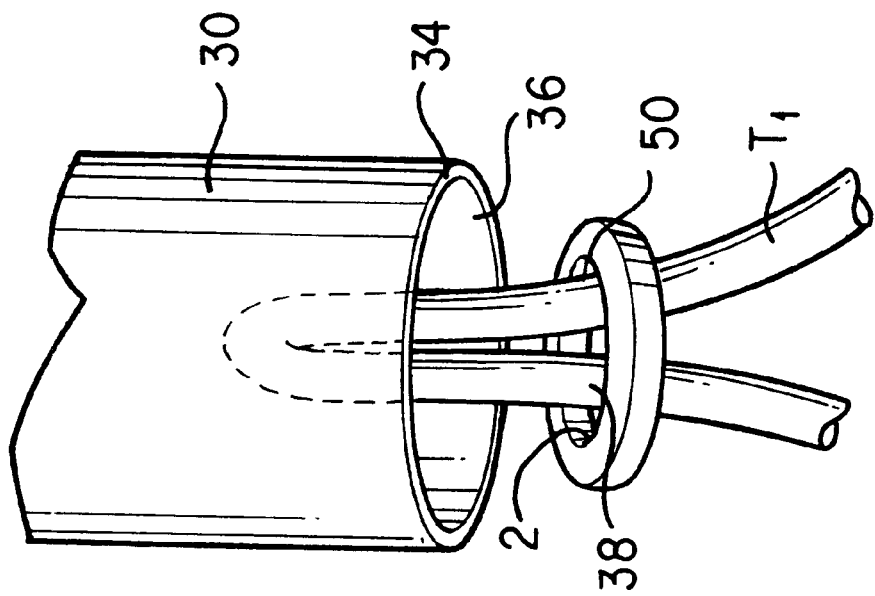
FIG. 9 is a perspective view of a portion of tissue with an elastic ligating band received thereon.
Figure 8:
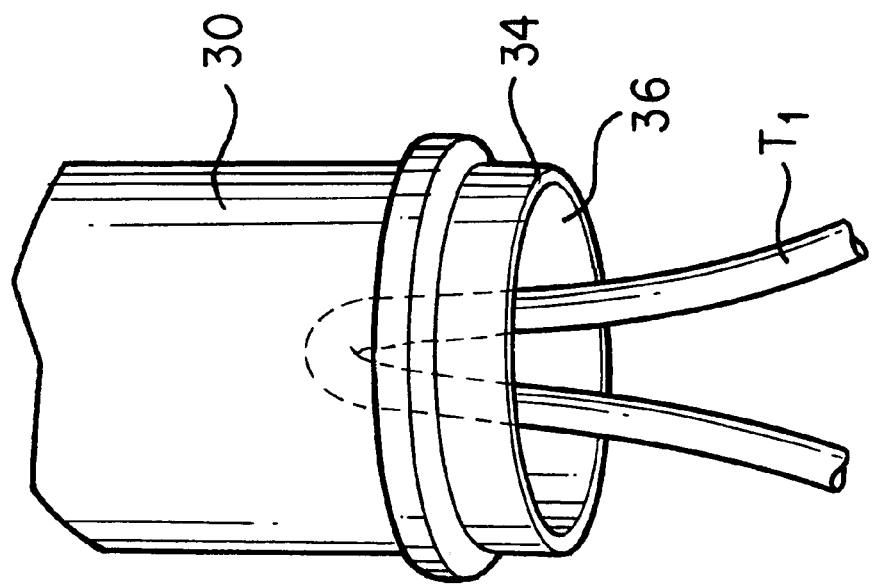
FIG. 8 is a perspective view of a portion of tissue drawn into a device for applying elastic ligating bands.

As shown in FIGS. 8 and 9, to apply ligating band 1 a physician first loads the band onto cylindrical support 32 of a ligating band dispenser 30, such as a trigger line ligating dispenser described above or such as a dispenser described in U.S. Pat. No. 5,356,416, so that the inner diameter ID of the ligating band 1 is substantially greater that its natural, predeformed inner diameter ID.

Next the physician positions distal end 34 having distal aperture 36 of the ligating band dispenser 30 adjacent to a first portion 38 of tissue T1. The first portion 38 is then drawn into the distal aperture 36, preferably under suction. Alternatively, the first section of tissue T1 may be drawn within the distal aperture 36 by mechanical means, such as a forceps, jaws, clamp, or the like (not shown). The physician then triggers the ligating band dispenser 30 to release one or more ligating bands 1 off of distal end 34 over the targeted first portion 38 of tissue T1.

As seen in FIG. 9, when the ligating band 1 has been dispensed from the ligating band dispenser 30, the inner diameter ID of the ligating band 1 suddenly decreases as the ligating band 1 seeks to return to its pre-deformed state. As the inner diameter ID decreases, the texturing 50 on the inner surface 2 of the ligating band 1 engages first portion 38 of tissue T1 and exerts inward pressure on the tissue. In embodiments of the invention having texturing 50 on inner surface 2, the texturing provides additional grip for engaging tissue T1. The pressure on the tissue stops all circulation through the targeted tissue T1, thereby causing first portion 38 to die. The body then sloughs off the dead tissue 38. Alternatively, the dead tissue 38 may be removed by mechanical means and aspirated into an endoscope, the ligating band dispenser 30, or a similar device.

In embodiments of the invention having texturing 50, while the texturing 50 on the inner surface 2 of the ligating band 1 is exerting inward pressure on the tissue 36, the texturing 50 restricts the movement of the ligating band 1 over the tissue 36. Thus, the ligating band 1 of the present invention is less likely than prior art ligating bands to be displaced from the targeted tissue portion 38 in response to outward pressures caused by the "pinching" of the targeted tissue portion 38 or by the movement of blood or other fluid through the targeted tissue T1. In addition, when the texturing 50 on the inner surface 2 of the ligating band 1 is exerting inward pressure on tissue portion 38, it is preferable that the texturing 50 on the first side 18 of the inner surface 2 remotely engages the texturing 50 on the second side 20 of the inner surface 2 through tissue portion 38 to form an interlocking pattern. By forming such an interlocking pattern, the texturing 50 more effectively restricts the movement of the ligating band 1 relative to tissue portion 38.

Still other objects and advantages of the present invention will become readily apparent to those skilled in the art from the detailed description, wherein the preferred embodiment and several alternate embodiments of the invention have been shown and described. The description of the preferred embodiment is simply by way of illustration of the best mode contemplated for carrying out the invention. As will be realized, the invention is capable of other and different embodiments, and its several details are capable of modification in various respects, all without departing from the invention. Accordingly, the drawings and descriptions are to be regarded as illustrative in nature, and not as restrictive of the invention which is to be limited only by the claims appended hereto.

What we claim is:

1. A method of ligating tissue within a living body comprising the steps of:

positioning adjacent to a portion of tissue to be ligated, an elastic band which has been stretched to increase a diameter of a central opening extending therethrough, wherein the central opening defines an axis, and wherein the ligating band comprises a continuous ring, the ring including a first curved edge formed between a first surface extending substantially parallel to the axis and a second surface extending substantially perpendicular to the axis;

drawing a portion of tissue to be ligated through the central opening of the elastic band; and releasing the elastic band so that the diameter of the central opening decreases to grip the tissue received therein.

2. The method according to claim 1, wherein a curved portion of the cross-section is located at an edge formed between at least one side surface of the elastic band extending substantially perpendicular to the axis and one of an inner longitudinal side thereof extending substantially parallel to the axis and an outer longitudinal side thereof extending substantially parallel to the axis.

3. The method according to claim 1, wherein a first surface of the elastic band includes a plurality of projections extending therefrom.

4. The method according to claim 1, wherein a first surface of the elastic band includes a plurality of depressions formed therein.

* * * * *